United States Patent
Turner et al.

(10) Patent No.: US 10,729,861 B2
(45) Date of Patent: Aug. 4, 2020

(54) METERED DOSE INHALER

(71) Applicant: Presspart GmbH & Co. KG, Marsberg (DE)

(72) Inventors: Richard Turner, Simonstone (GB); Benjamin Jung, Köln (DE); Dana Shears, Cary, NC (US); Hans-Peter Schmelzer, Meerbusch (DE); David Hibbard, Bedford, NH (US); Dean H. Owens, Hooksett, NH (US); Joseph St Onge, Raymond, NH (US); Hannah Bond, Manchester, NH (US); Benjamin Glace, Hampstead, NH (US); Douglas Browne, Groton, MA (US); Karl Edward Robinson, Barnard Castle Durham (GB)

(73) Assignee: Presspart GmbH & Co. KG, Marsberg (DE)

( * ) Notice: Subject to any disclaimer, the term of this patent is extended or adjusted under 35 U.S.C. 154(b) by 295 days.

(21) Appl. No.: 15/716,784

(22) Filed: Sep. 27, 2017

(65) Prior Publication Data
US 2018/0093053 A1     Apr. 5, 2018

(30) Foreign Application Priority Data
Sep. 30, 2016 (EP) .................................... 16191743

(51) Int. Cl.
*A61M 15/00* (2006.01)
*B65D 83/54* (2006.01)

(52) U.S. Cl.
CPC ...... *A61M 15/0068* (2014.02); *A61M 15/007* (2014.02); *A61M 15/008* (2014.02);
(Continued)

(58) Field of Classification Search
CPC . A61M 15/0068; A61M 11/02; A61M 15/007
(Continued)

(56) References Cited

U.S. PATENT DOCUMENTS 6,752,153 B1   6/2004 Eckert
9,517,314 B2* 12/2016 Hately .................. G06M 1/166
(Continued)

FOREIGN PATENT DOCUMENTS

DE     29814647 U1   12/1999
GB     2506385 A     4/2014
(Continued)

OTHER PUBLICATIONS

European communication dated Mar. 6, 2017 in corresponding European patent application No. 16191743.0.
(Continued)

*Primary Examiner* — Kendra D Carter
*Assistant Examiner* — Suraj Kandalam
(74) *Attorney, Agent, or Firm* — Nields, Lemack & Frame, LLC (57) ABSTRACT

A metered dose inhaler (1) for dispensing aerosol doses comprises an actuation housing (2) adapted to receive a canister (4). The canister (4) is configured to move from a rest position to an activation position in which a valve (7) of the canister (4), positioned at a valve end (8) of the canister (4), is depressed against a bottom portion of the actuation housing such that an aerosol dose is released. The inhaler (1) further comprises a mechanical dose (10) counter comprising an indicator member which is constructed and arrangement to undergo a predetermined count-indicating motion when an aerosol dose is released. Moreover, the inhaler (1) comprises a triggering unit (11) for triggering at least one electrical switch (12) when the canister (4) is moved from the rest position to the activation position whereby an
(Continued)

electrical signal is generated. Also part of the inhaler (1) is a processing unit for processing the signal generated by the switch (12) upon being triggered.

13 Claims, 5 Drawing Sheets

(52) U.S. Cl.
CPC ........... *A61M 15/009* (2013.01); *B65D 83/54* (2013.01); *A61M 15/0086* (2013.01); *A61M 2205/33* (2013.01); *A61M 2205/3584* (2013.01); *A61M 2205/3592* (2013.01); *A61M 2205/502* (2013.01); *A61M 2205/8206* (2013.01)

(58) Field of Classification Search
USPC ...................................................... 453/30, 58
See application file for complete search history.

(56) References Cited

U.S. PATENT DOCUMENTS

| | | | | |
|---|---|---|---|---|
| 9,943,656 | B2 * | 4/2018 | Shears | .............. A61M 15/0083 |
| 2002/0195102 | A1 | 12/2002 | Rand et al. | |
| 2006/0243275 | A1 * | 11/2006 | Ruckdeschel | ..... A61M 15/0091 |
| | | | | 128/200.23 |
| 2007/0056585 | A1 * | 3/2007 | Davies | .............. A61M 15/0065 |
| | | | | 128/203.15 |
| 2010/0192948 | A1 * | 8/2010 | Sutherland | ........ A61M 15/0065 |
| | | | | 128/203.15 |
| 2011/0253139 | A1 | 10/2011 | Guthrie et al. | |
| 2013/0098941 | A1 * | 4/2013 | Wegelin | ................ B05B 12/004 |
| | | | | 222/23 |
| 2018/0221600 | A1 * | 8/2018 | Shears | ................... A61M 11/00 |

FOREIGN PATENT DOCUMENTS

| | | |
|---|---|---|
| WO | 97/13553 A1 | 4/1997 |
| WO | 2005/009325 A2 | 2/2005 |
| WO | 2007/045904 A1 | 4/2007 |
| WO | 2007/088367 A1 | 8/2007 |
| WO | 2011/071788 A1 | 6/2011 |
| WO | 2011/083377 A1 | 7/2011 |
| WO | 2013/043063 A1 | 3/2013 |
| WO | 2014/039367 A1 | 3/2014 |
| WO | 2016/030844 A1 | 3/2016 |

OTHER PUBLICATIONS

European communication dated Sep. 19, 2019 in corresponding European patent application No. 16191743.0.

* cited by examiner

METERED DOSE INHALER

The present invention relates to a metered dose inhaler for dispensing aerosol doses comprising an actuation housing adapted to receive a canister. The canister is configured to move from a rest position to an activation position in which a valve of the canister, positioned at a valve end of the canister, is depressed against a bottom portion of the actuation housing such that an aerosol dose is released. The inhaler further comprises a mechanical dose counter comprising an indicator member which is constructed and arranged to undergo a predetermined count-indicating motion when an aerosol dose is released.

BACKGROUND OF THE INVENTION

Metered dose inhalers (MDIs) are medication delivery devices that are often used to deliver a pharmaceutical formulation including one or more pharmaceutically active compounds to a human or other mammalian patient.

Typically, the pharmaceutical formulation is delivered by the MDIs in unit doses in the form of an aerosol. Each actuation of the MDI delivers one unit dose. The unit dose is expelled by the MDI and is taken into the body of the patient upon inhalation, via the nose or mouth. The pharmaceutical formulation is then delivered to the lungs of the patient. Metered dose inhalers are typically used for the treatment of respiratory infections and disorders including respiratory tract infections, obstructive lung disease, inflammatory lung disease and chronic obstructive pulmonary disease. Asthma treatment is a particularly commonly use of MDIs.

Such an MDI is for example disclosed in WO 2011/071788 A1. The inhaler comprises a mechanical dose counter having an indicator member which undergoes predetermined count-indicating motion when a dose is dispensed from the inhaler.

An alternative arrangement is disclosed in WO 2016/030844 A1. This document describes a metered dose inhaler having trigger members which upon depression of a canister trigger electrical switches thereby counting doses being released from the canister.

In the field of MDIs, it is desired to provide the inhalers not only with a counting function in order to count the dispensed or remaining doses but also with additional functions such as monitoring functions or evaluation functions. Based on these additional functions the physician or patient may for example monitor the frequency of dispensed doses and the point of time when these doses have been dispensed. Experience shows that it is difficult to confirm the reliability of the dose counting function when providing inhalers with such additional monitoring functions.

SUMMARY OF THE INVENTION

It is an object of the present invention to provide an inhaler that overcomes the above-mentioned problem. In particular, it is an object of the present invention to provide a metered dose inhaler with a reliable dose counting function as well as additional functions such as monitoring functions. Another object of the invention is to provide a triggering unit that allows the implementation of these afore-mentioned additional functions in the metered dose inhaler.

The above-mentioned object is achieved by a metered dose inhaler comprising the features of claim 1. Preferred embodiments are set up in the dependent claims.

According to the present invention, the metered dose inhaler comprises a mechanical dose counter having an indicator member which is constructed and arranged to undergo a predetermined count-indicating motion when an aerosol dose is released and further comprises a triggering unit for triggering at least one electrical switch when the canister is moved from a rest position to the activation position, whereby an electrical signal is generated. Moreover, the metered dose inhaler comprises a processing unit for processing the signal generated by the switch upon being triggered.

The advantage of providing the MDI with a triggering unit as well as a processing unit in addition to a mechanical dose counter is that the dose counting function is reliably provided by the mechanical dose counter wherein additional functions such as monitoring or evaluation functions may be realized by the additional triggering unit as well as the processing unit. As the mechanical dose counter has proven its reliability in millions of inhalers being available on the market the risks of dose counting failures are mitigated to a high degree.

Moreover, as the mechanical dose counter shows the remaining doses its combination with the triggering unit as well as the processing unit has the ability to circumvent the need of an electrical display for displaying the counted doses. For example the actuation housing may comprise an opening through which the patient is able to see the indicator member of the mechanical dose counter displaying the number of remaining doses. Thus, battery power can be saved and therewith either the battery size can be reduced or the shelf life can be improved.

As the combination makes it possible to separate the dose counting function and evaluation of the quality of dose actuation function, both functions of the MDI can be independently optimized. For example the position of the canister when the dose is released might not be the best position where a high quality of actuation of the dose counter is provided. Moreover, this position of the canister might also not be ideal to actuate the triggering unit as well as the processing unit.

Preferably the evaluation function of the electrical unit may be adapted to evaluate whether the MDI has been used correctly by measuring the velocity and/or the holding time of the canister being depressed. Preferably, when the velocity and/or the holding time are within a predefined range, the canister has been actuated correctly.

In an embodiment of the present invention the triggering unit, the at least one switch and the processing unit are mounted inside the actuation housing.

In a preferred embodiment, the metered dose inhaler further comprises a transmitting unit for wirelessly transmitting results processed by the processing unit. Optionally, the transmitting unit may be capable of transmitting the results via radio frequency or Bluetooth. Preferably, the results may be transmitted to a user's smartphone or any other electronic device. Optionally, the MDI comprises a printed circuit board (PCB) on which electrical components such as the at least one switch, the processing unit and the transmitting unit are positioned.

Also preferred is an embodiment according to which the triggering unit comprises trigger members for triggering the at least one electrical switch, wherein the trigger members are designed as flexible tongues each having an end portion. Optionally, the triggering unit comprises two trigger members which each trigger one electrical switch. Thus, it is possible to trigger the velocity of the canister being depressed by the user. Optionally, the switches are dome switches having a dome-like shape in order to reliably detect triggering of the trigger members.

Optionally, the end portions of the trigger members comprise an upper side facing away from the bottom portion of the actuation housing and being adapted to form a contact surface for the canister when being depressed, wherein the end portions of the trigger members further comprise a curved end face, adapted to abut a ferrule of the canister positioned at its valve end. Optionally the curved end face may be realized by a curved shaped chamfer or by the end face having at least a partially curved shape. Also a combination of a curved chamfer together with a at least partially curved end face may be realized.

Preferably, the canister hits the end portions of the trigger members when being depressed thereby deforming the trigger members which each trigger the corresponding electrical switch. Preferably, the trigger members are arranged such that the canister hits the end portions of the corresponding trigger members one after the other such that the electrical signals are generated sequentially.

In another arrangement each end portion of the trigger members further comprises two side surfaces, wherein the upper side of the end portions is wider than the side surfaces such that each end portion has a rectangular cross-section. As the upper side of the end portion is wider than the side surfaces, the end portion forms a contact surface which is sufficient in size for being hit by the canister when being depressed whereas the lateral extension of the end portion lateral to the upper side towards the bottom portion of the housing does only need little space.

In a preferred embodiment, the actuation housing has a longitudinal axis, wherein the actuation housing is configured to receive the canister along the longitudinal axis, vertically above the mechanical dose counter. Preferably, the canister and the mechanical dose counter are aligned along the longitudinal axis such that the valve of the canister extends through the mechanical dose counter. This is a space saving arrangement.

Further preferred is an embodiment according to which the trigger members are designed such that the end portions of the trigger members are positioned along the longitudinal axis between the mechanical dose counter and the canister. Preferably, the ferrule of the canister comprises a first actuation surface and a second actuation surface. The ferrule contacts the mechanical dose counter when the canister is depressed with the first actuation surface whereas the second actuation surface contacts the upper side of the end portions during the movement of the canister from the rest position to the activation position. This is a very space saving arrangement and enables the combination of the mechanical dose counter and the electrical unit comprising the triggering unit and the processing unit in one single MDI.

Also preferred is an embodiment according to which the triggering unit further comprises a main plate which is vertically fixed in the actuation housing wherein the trigger members are integrally formed with the main plate as one piece. Preferably, the triggering unit is produced by injection molding which decreases the production costs. As the trigger members are integrally formed with the main plate, the whole triggering unit may be produced using one single mould. Additional assembly steps as connecting the trigger members to the main plate are omitted.

In a preferred embodiment, the main plate defines a vertical plane along which the main plate encloses an aperture, wherein the trigger members extend into the aperture. This increases the torsional stiffness of the main plate and thus the torsional stiffness of the triggering unit. Preferably, the trigger members extend at least partially along or parallel to the plane. Optionally the main plate may enclose two apertures, wherein each of the two trigger members at least partially extend in one of the apertures.

Optionally, the main plate has fixation elements for fixing a printed circuit board (PCB) with at least one electrical switch mounted thereon to the main plate such that the trigger members trigger the at least one electrical switch when the canister is depressed from the rest position to the activation position. As the printed circuit board is fixed to the triggering unit, assembly of the MDI is simplified. Preferably, the printed circuit board is inserted into the actuation housing together with and fixed to the triggering unit.

Preferably, the fixation elements are snap-in tongues which are designed to engage with the printed circuit board. This provides a secure and simple connection between the printed circuit board and the triggering unit.

Alternatively, the main plate has distance elements adapted to abut the printed circuit board and to keep the printed circuit board at a distance relative to the main plate. Thus, a predefined distance between the printed circuit board and the main plate is ensured in order to guarantee a reliable triggering of the electrical switches by the trigger members.

In a preferred arrangement, the actuation housing further comprises a mouthpiece for inhalation of the aerosol, wherein the triggering unit is positioned within the actuation housing opposite to the mouthpiece and, wherein the actuation housing is adapted to receive the canister in between the triggering unit and the mouthpiece. Compared to MDIs in which the printed circuit board is positioned in between the mouthpiece and the canister, the advantage of the present invention is that the mouthpiece may be shortened as the canister is positioned closer to the mouthpiece. Thus, the drug pathway of the aerosol can be designed in an aerodynamic efficient way such that the mouthpiece does not interfere the drug pathway. Deposits of the aerosol within the mouthpiece are omitted.

Preferably, the metered dose inhaler further comprises an electronic display on which results processed by the processing unit are displayed. Preferably the electronic display is a LCD or a LED-display. For example the batteries to power electrical components of the MDI might optionally not have to be replaced during the life cycle of the MDI. Optionally, in order to save energy the electronic display might be operable in a standby mode or may be switched off during nonuse. Only when a display is required, such as when only a few doses are left in the canister, or only upon a user request the electronic display may be switched on or woken up from the standby mode.

The object of the present invention is also solved by a triggering unit for triggering an electrical switch of a metered dose inhaler comprising the features of claim 15.

The triggering unit comprises a main plate adapted for vertical fixation in an inhalers actuation housing and trigger members for triggering at least one switch when a canister of the inhaler is depressed from a rest position to an activation position. The Trigger members are integrally formed with the main plate and are designed as flexible tongues each having an end portion. The end portions extend away from the main plate and are tilted relative to it. The end portions comprise an upper side adapted to form a contact surface for the canister when being depressed. The end portions comprise a curved end face adapted to abut a ferrule of the canister.

The triggering unit according to the present invention may be used in combination with the metered dose inhaler as described above. Preferably, the triggering unit may also be used with any other metered dose inhaler.

DETAILED DESCRIPTION OF THE INVENTION

The invention is further described by referring to the appended figures which show preferred embodiments and shall by no means limit the present invention.

Figure 1:
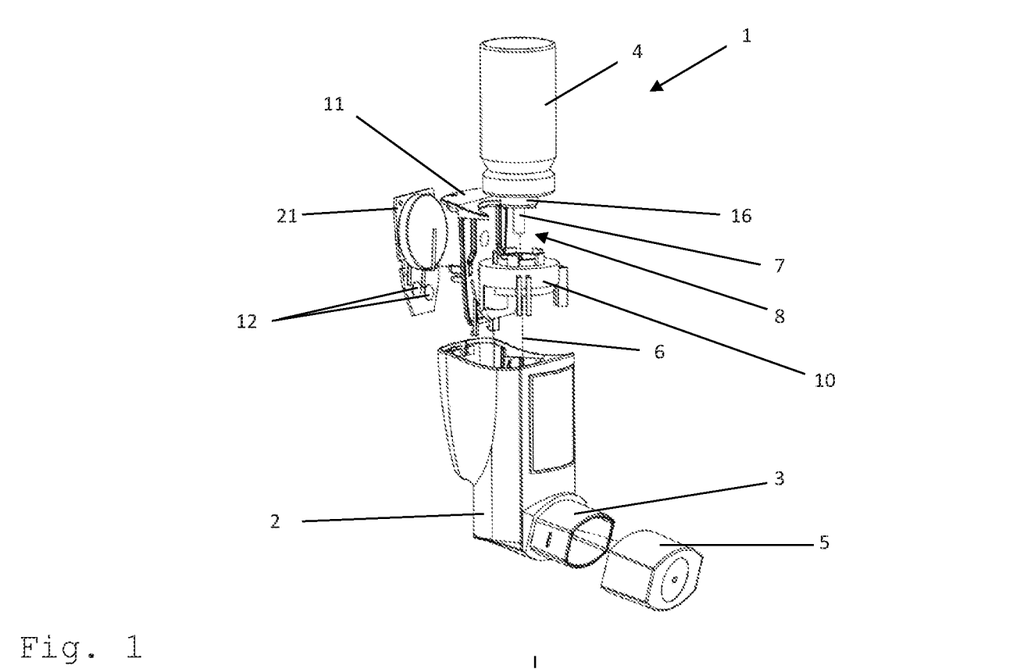
FIG. 1 shows a perspective exploded view of a metered dose inhaler according to the present invention.
Figure 2:
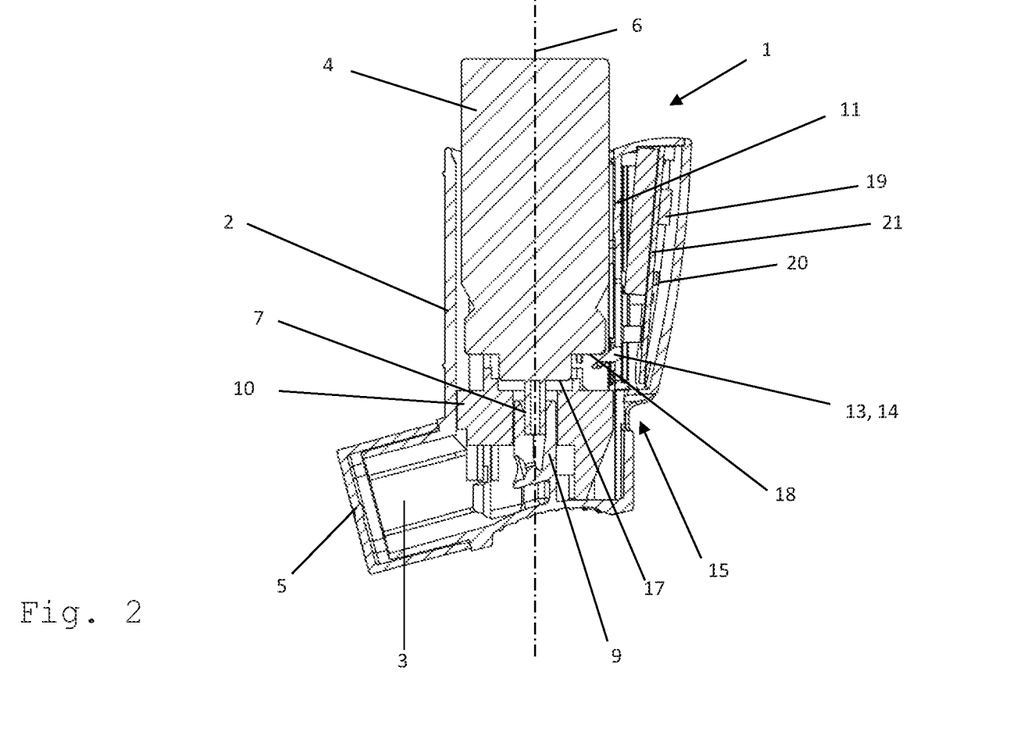
FIG. 2 shows a sectional view of an assembled metered dose inhaler.

Referring to FIGS. 1 and 2, a metered dose inhaler (MDI) 1 for dispensing aerosol doses comprises an actuation housing 2 with a mouthpiece 3 through which a patient inhales a pharmaceutical formulation contained in a canister 4. During nonuse of the MDI 1, the mouthpiece 3 may be covered by a cap 5. The actuation housing 2 has a longitudinal axis 6 along which the actuation housing 2 is configured to receive the canister 4.

The canister 4 comprises a valve 7 positioned at its valve end 8. The canister 4 is configured to move from a rest position to an activation position. During nonuse of the MDI 1 the canister 4 remains in a rest position as shown in FIG. 2. When being depressed by the patient, the canister 4 moves from the rest position to an activation position, in which the valve 7 is depressed against a bottom portion 9 of the actuation housing 2 such that an aerosol dose is released.

The MDI 1 further comprises a mechanical dose counter 10 comprising an indicator member (not shown) which is constructed and arranged to undergo a predetermined count-indication motion when an aerosol dose is released. The indicator member may comprise members which for example show the number of remaining doses contained in the canister 4 and which can be seen through an opening (not shown) in the actuation housing 2. The mechanical dose counter 10 is positioned along the longitudinal axis 6 vertically below the canister 4. In other words, the actuation housing 2 is configured to receive the canister 4 along the longitudinal axis 6 vertically above the mechanical dose counter 10.

The MDI 1 further comprises a triggering unit 11 triggering electrical switches 12 when the canister 4 is moved from the rest position to the activation position whereby an electrical signal is generated. The triggering unit 11 is positioned within the actuation housing 2 opposite to the mouthpiece 3 such that the canister 4 is received in the actuation housing 2 in between the triggering unit 11 and the mouthpiece 3.

The triggering unit 11 comprises two trigger members 13 for triggering the two electrical switches 12. The trigger members 13 are designed as flexible tongues 14 each having an end portion 15. The trigger members 13 are designed such that the end portions 15 of the trigger members 13 are positioned along the longitudinal axis 6 between the mechanical dose counter 10 and the canister 4.

The canister 4 comprises at its valve end 8 a ferrule 16 having a first actuation surface 17 for acting on the dose counter 10 and a second actuation surface 18 for acting on the trigger members 13. When the canister 4 is moved from the rest position to the activation position the first actuation surface 17 hits the mechanical dose counter 10 thereby undergoing a predetermined count indication motion. Moreover, during the same movement, the second actuation surface 18 hits the end portion 15 of the trigger members 13 thereby deforming the trigger members 13 such that the trigger members 13 bend in a lateral direction to the longitudinal axis 6 and trigger the electrical switches 12.

The MDI 1 further comprises a processing unit 19 for processing the signal generated by the switches 12 upon being triggered by the trigger members 13. The results generated thereby may be wirelessly transmitted to another device such as a smartphone or any other electronic device by a transmitting unit 20.

The MDI 1 further comprises a printed circuit board (PCB) 21 on which electrical components such as the switches 12, the processing unit 19 and the transmitting unit 20 are positioned. The PCB 21 is fixed in a certain distance relative to the triggering unit to the same such that the trigger members trigger the electrical switches 12 when the canister 4 is depressed from the rest position to the activation position. The PCB 21 is mounted together with the triggering unit 11 into the actuation housing 2. In other words: The triggering unit 11, the switches 12 and the processing unit 19 are mounted inside the actuation housing 2.

The triggering unit 11, the switches 12 and the processing unit 19 form an electronic monitoring and evaluation device for monitoring and evaluating the use of the metered dose inhaler, wherein the electronic monitoring and evaluating device and the mechanical dose counter 10 are positioned inside the actuation housing 2. Preferably, the monitoring and evaluation device is adapted to evaluate whether the MDI has been used correctly by measuring the velocity and/or the holding time of the canister being depressed. Optionally, when the velocity and/or the holding time are within a predefined range, the canister has been actuated correctly.

Figure 3:
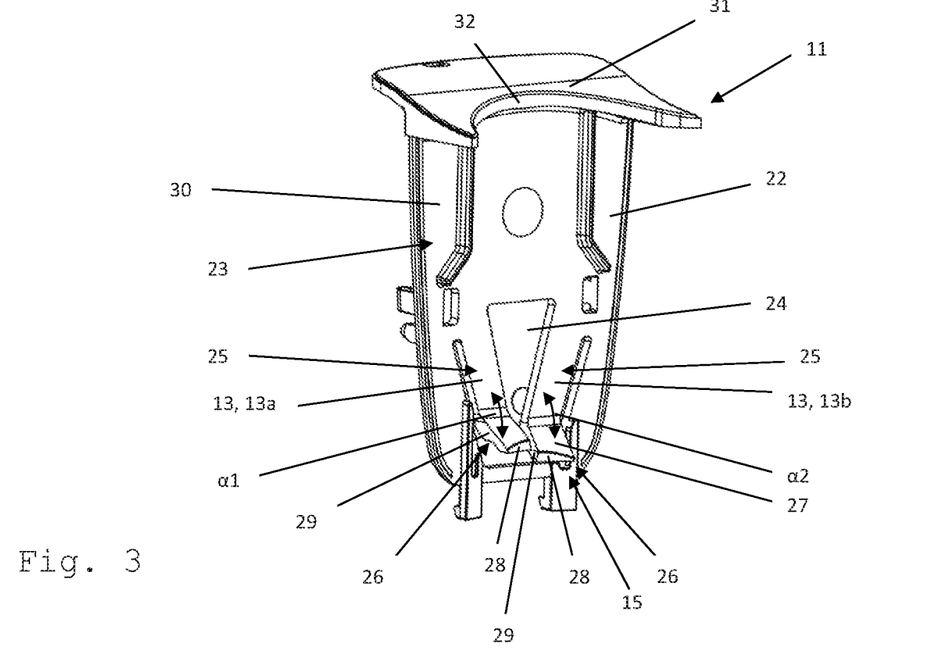
FIG. 3 shows a perspective front view of a triggering unit.
Figure 4:
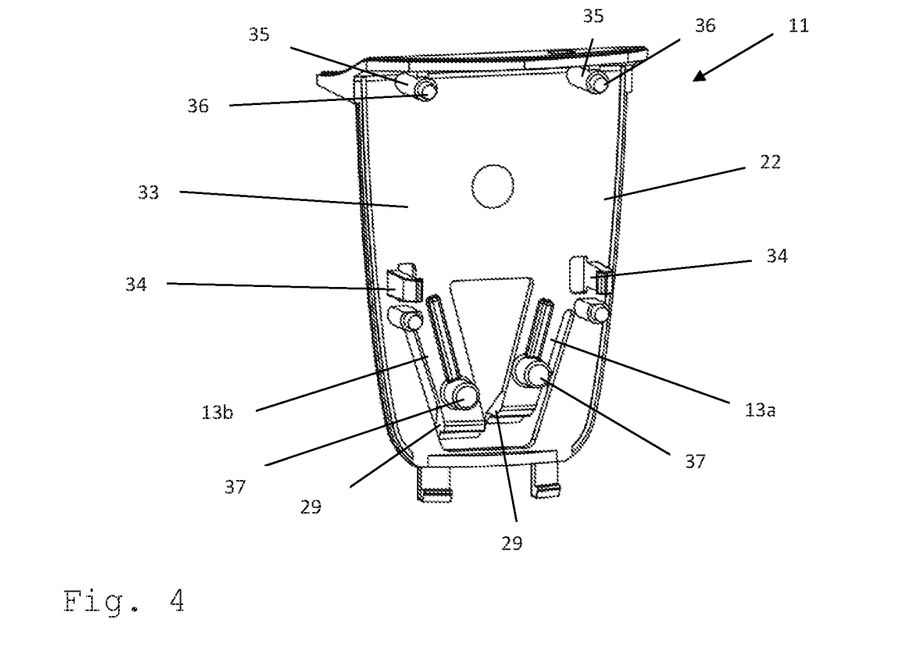
FIG. 4 shows a perspective rear view of the triggering unit according to FIG. 3.

FIGS. 3 and 4 show the triggering unit 11 in more detail. The triggering unit 11 comprises a main plate 22 which is vertically fixed in the actuation housing 2 (FIG. 2), wherein the trigger members 13 are integrally formed with the main plate 22 as one piece. The main plate 22 defines a vertical plane 23 along which the main plate 22 encloses an aperture 24. The trigger members 13 partially extend along the plane 23 into the aperture 24.

The triggering unit 11 comprises a first trigger member 13a and a second trigger member 13b each having a first section 25 and a second section 26. The first sections 25 connect the second sections 26 to the main plate 22. The first sections 25 extend along the plane 23 and are tilted towards an imaginary vertical axis. Each trigger member 13a, 13b has a substantially L-shape.

The second sections 26 of the trigger members 13a, 13b form the end portions 15 which comprise an upper side 27 facing away from the bottom portion 9 (FIG. 2) of the actuation housing 2 (FIG. 2). The upper side 27 is adapted to form a contact surface for the canister 4 (FIG. 2) when being depressed. Moreover, the end portions 15 comprise a curved end face 28 adapted to abut the ferrule 16 (FIG. 1) of the canister 4 positioned at its valve end 8 (FIG. 1).

Each end portion 15 of the trigger members 13a, 13b further comprises two side surfaces 29, wherein the upper side 27 of the end portions 15 is wider than the side surfaces 29 such that each end portion 15 has a rectangular cross-section.

On a front side 30 of the main plate 22 the second sections 26 of the trigger members 13a, 13b are tilted relative to the main plate 22. The first section 25 and the second section 26 of the first trigger member 13a enclose a first angle α1 and the first section 25 and the second section 26 of the second trigger member 13b enclose a second angle α2. The first angle α1 and the second angle α2 differ from each other. Moreover, the first section 25 of the first trigger member 13a is in its vertical extension shorter than the first section 25 of the second trigger member 13b.

The triggering unit 11 comprises at its top a cover 31 for partially covering the actuation housing 2 (FIG. 2). The cover 31 comprises a curved side face 32 which is formed according to the outer measurements of the canister 4 (FIG. 1).

At its rear side 33 the main plate 22 comprises fixation elements 34 for fixing the PCB 21 (FIG. 1) to the main plate 22. The fixation elements 34 are snap-in tongues which are designed to engage with the PCB 21.

Moreover, the main plate 22 comprises distance elements 35 at its rear side 33 adapted to abut the PCB 21 and to keep the PCB 21 at a distance relative to the main plate. The distance elements 35 are formed as posts which extend from the rear side 33 of the main plate 22 and comprise an abutment face 36 adapted to abut the PCB 21 (FIG. 1).

As can be seen in particular in FIG. 4, the trigger members 13a, 13b each comprise a bumper 37 at their rear side 33 for triggering the switches 12 (FIG. 1).

Figure 5:
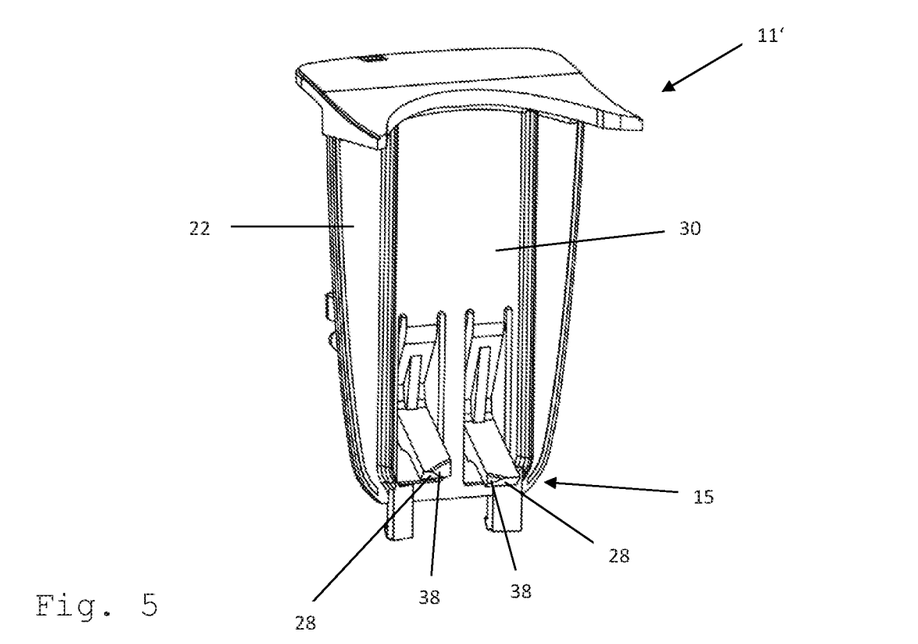
FIG. 5 shows a perspective front view of a second embodiment of the triggering unit.
Figure 6:
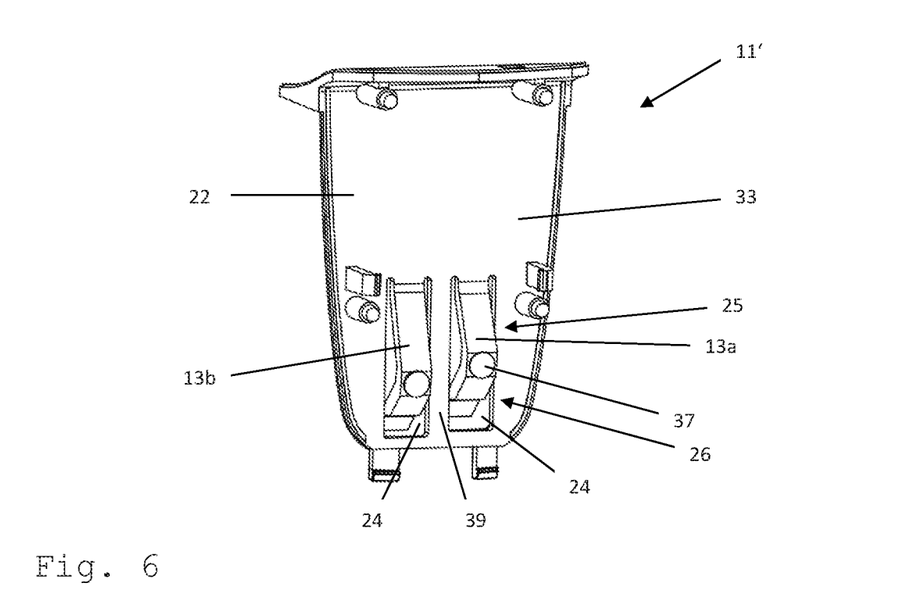
FIG. 6 shows a perspective rear view of the triggering unit according to FIG. 5.

FIGS. 5 and 6 show a second embodiment of the triggering unit 11. The triggering unit 11' differs from the one shown in the FIGS. 3 and 4 by the shape of the trigger members 13a, 13b. As shown in particular in FIG. 6, the first sections 25 of the trigger members 13a, 13b extend away from the rear side 33 of the main plate 22 wherein the second sections 26 of the trigger members 13a, 13b extend from the first sections 25 through the apertures 24 towards the front side 30 of the main plate 22.

Moreover, the end portions 15 of the trigger members 13a, 13b each comprise a curved chamfer 38 which partially extends at each end face 28. Additionally, the main plate 22 has a rip 39 which extends vertically between the trigger members 13a, 13b and separates the apertures 24 from each other. The trigger members 13a, 13b partially extend parallel to the main plate 22, in particular in the area of their bumpers 37.

Figure 7:
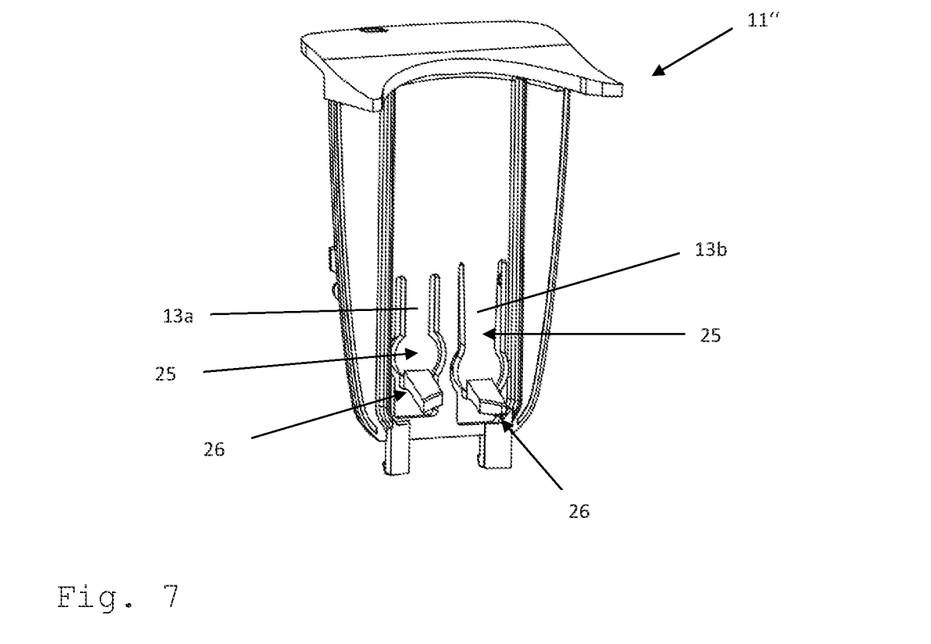
FIG. 7 shows a perspective front view of a third embodiment of the triggering unit.
Figure 8:
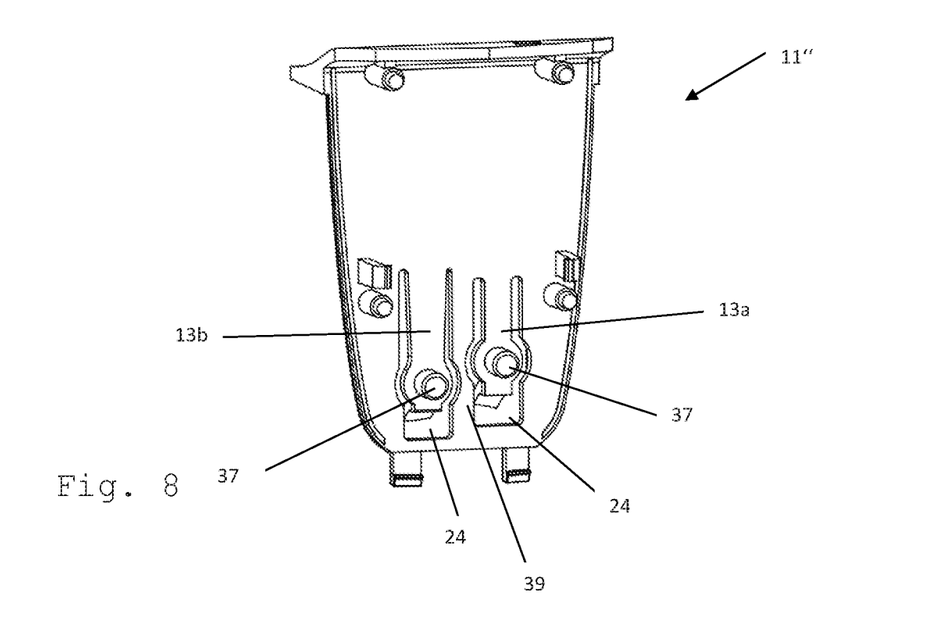
FIG. 8 shows a perspective rear view of the triggering unit according to FIG. 7.

FIGS. 7 and 8 show a third embodiment of the triggering unit 11. The triggering unit 11" differs from the one shown in FIGS. 3 and 4 by the first sections 25 of the trigger members 13a, 13b which extend vertically towards the second portions 26. In the area of their bumpers 37 the trigger members 13a, 13b have an approximate circular shape. A rip 39 vertically divides the apertures 24. The first sections 25 of the trigger members 13a, 13b extend parallel to an imaginary vertical axis.

Figure 9:
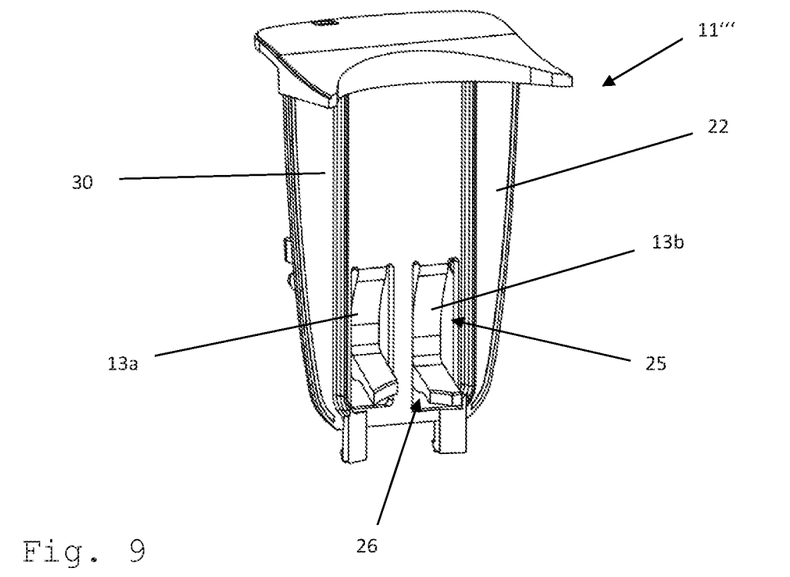
FIG. 9 shows a perspective front view of a fourth embodiment of the triggering unit.
Figure 10:
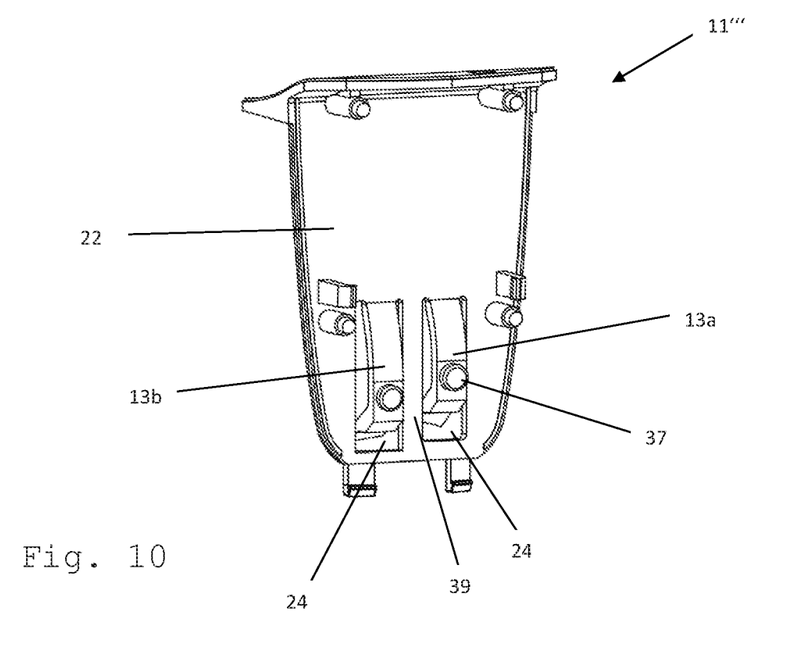
FIG. 10 shows a perspective rear view of the triggering unit according to FIG. 9.

FIGS. 9 and 10 show a fourth embodiment of the triggering unit 11. The triggering unit 11''' differs from the one shown in FIGS. 3 and 4 by the run of the trigger members 13a, 13b. The first sections 25 of the trigger members 13a, 13b extend in FIG. 10 rearwards in a curved manner such that the area of the first sections 25, close to the bumpers 37, is parallel to the main plate 22. The second sections 26 of the trigger members 13a, 13b extend from the first sections 25 through the aperture 24 towards the front side of the main plate 22. A rip 39 divides the aperture 24.

It has to be understood that the triggering unit 11, 11', 11", 11''' as detailed shown in the FIGS. 3 to 10 in detail may be used in combination with the MDI 1 as disclosed in FIGS. 1 and 2 but also in combination with any other inhaler.

The invention claimed is:

1. Metered dose inhaler for dispensing aerosol doses comprising:
    an actuation housing adapted to receive a canister which is configured to move from a rest position to an activation position in which a valve of the canister, positioned at a valve end of the canister, is depressed against a bottom portion of the actuation housing such that an aerosol dose is released and
    a mechanical dose counter comprising an indicator member which is constructed and arranged to undergo a predetermined count-indicating motion when an aerosol dose is released,
    wherein the metered dose inhaler further comprises a triggering unit comprising trigger members for triggering at least one electrical switch when the canister is moved from the rest position to the activation position, whereby an electrical signal is generated, and
    a processing unit for processing the signal generated by the switch upon being triggered; and
    wherein the trigger members are designed as flexible tongues each having an end portion; wherein the end portions of the trigger members comprise an upper side facing away from the bottom portion of the actuation housing and being adapted to form a contact surface for the canister when being depressed, and wherein the end portions of the trigger members further comprise a curved end face, adapted to abut a ferrule of the canister positioned at its valve end;
    wherein the actuation housing further comprises a mouthpiece for inhalation of the aerosol and wherein the triggering unit is positioned within the actuation housing opposite to the mouthpiece, and wherein the actuation housing is adapted to receive the canister in between the triggering unit and the mouthpiece.

2. Metered dose inhaler according to claim 1, wherein the metered dose inhaler further comprises a transmitting unit for wirelessly transmitting results processed by the processing unit.

3. Metered dose inhaler according to claim 1, wherein each end portion of the trigger members further comprises two side surfaces, and wherein the upper side of the end portions is wider than the side surfaces such that each end portion has a rectangular cross section.

4. Metered dose inhaler according to claim 1, wherein the trigger members are designed such that the end portions of the trigger members are positioned along the longitudinal axis between the mechanical dose counter and the canister.

5. Metered dose inhaler according to claim 1, wherein the triggering unit further comprises a main plate which is vertically fixed in the actuation housing, and wherein the trigger members are integrally formed with the main plate as one piece.

6. Metered dose inhaler according to claim 5, wherein the main plate has fixation elements for fixing a printed circuit board with at least one electrical switch to the main plate such that the trigger members trigger the at least one electrical switch when the canister is depressed from the rest position to the activation position.

7. Metered dose inhaler according to claim 6, wherein the fixation elements are snap-in tongues which are designed to engage with the printed circuit board.

8. Metered dose inhaler according to claim 6, wherein the main plate has distance elements adapted to abut the printed circuit board and to keep the printed circuit board at a distance relative to the main plate.

9. Metered dose inhaler according to claim 1, wherein the main plate defines a vertical plane along which the main plate encloses at least one aperture, and wherein the trigger members extend into the at least one aperture.

10. Metered dose inhaler according to claim 1, wherein the actuation housing has a longitudinal axis, and wherein the actuation housing is configured to receive the canister along the longitudinal axis, vertically above the mechanical dose counter.

11. Metered dose inhaler according to claim 10, wherein the trigger members are designed such that the end portions of the trigger members are positioned along the longitudinal axis between the mechanical dose counter and the canister.

12. Metered dose inhaler according to claim 1, wherein the metered dose inhaler further comprises an electronic display on which results are displayed, which have been processed by the processing unit.

13. Triggering unit for triggering an electrical switch of a metered dose inhaler comprising:
- a main plate adapted for vertical fixation in an metered dose inhaler's actuation housing and
- trigger members for triggering at least one switch when a canister of the metered dose inhaler is depressed from a rest position to an activation position,
- wherein the trigger members are integrally formed with the main plate and are designed as flexible tongues each having an end portion,
- wherein the end portions extend away from the main plate and are tilted relative to it and,
- wherein the end portions comprise an upper side adapted to form a contact surface for the canister when being depressed,
- wherein
- the end portions comprise a curved end face adapted to abut a ferrule of the canister.

* * * * *